US00PP35870P2

(12) United States Plant Patent
Renner

(10) Patent No.: US PP35,870 P2
(45) Date of Patent: Jun. 11, 2024

(54) ***CUPHEA* PLANT NAMED 'FLORCUMY05'**

(50) Latin Name: *Cuphea hyssopifolia*
Varietal Denomination: FLORCUMY05

(71) Applicant: Florensis B.V., Hendrik-Ido-Ambacht (NL)

(72) Inventor: Johann Renner, Seekirchen am Wallersee (AT)

(73) Assignee: Florensis B.V., Hendrik-Ido-Ambacht (NL)

( * ) Notice: Subject to any disclaimer, the term of this patent is extended or adjusted under 35 U.S.C. 154(b) by 0 days.

(21) Appl. No.: 18/387,897

(22) Filed: Nov. 8, 2023

(51) Int. Cl.
*A01H 5/02* (2018.01)
*A01H 6/00* (2018.01)

(52) U.S. Cl.
USPC ..... Plt./420

(58) Field of Classification Search
USPC ..... Plt./420
See application file for complete search history.

*Primary Examiner* — Susan McCormick Ewoldt
(74) *Attorney, Agent, or Firm* — Aubrey Charles

(57) ABSTRACT

A new and distinct cultivar of *Cuphea* plant named 'FLORCUMY05', characterized by its medium purple-colored flowers, dark green-colored foliage, and moderately vigorous, upright growth habit, is disclosed.

1 Drawing Sheet

Latin name of genus and species of plant claimed: *Cuphea hyssopifolia.*
Variety denomination: 'FLORCUMY05'.

BACKGROUND OF THE INVENTION

The present invention relates to a new and distinct cultivar of *Cuphea* plant botanically known as *Cuphea hyssopifolia* and hereinafter referred to by the cultivar name 'FLORCUMY05'.

The new cultivar originated in a controlled breeding program in Neumarkt am Wallersee Austria during August 2019. The objective of the breeding program was the development of *Cuphea* cultivars that are highly floriferous with attractive flower colors and a well-branched, spreading growth habit.

The new *Cuphea* cultivar is the result of open-pollination. The female (seed) parent of the new cultivar is 'Cupid Purple', not patented, characterized by its medium purple-colored flowers, dark green-colored foliage, and moderately vigorous, upright growth habit. Based on location in the field, the male (pollen) parent of the new cultivar is most likely to be MYRTIS Deep Pink 'FLORCUMY38', not patented, characterized by its deep pink-colored flowers, dark green-colored foliage, low growth vigor, and upright growth habit. The new cultivar was selected as a single flowering plant within the progeny of the above stated open-pollination August 2020 in a controlled environment in Neumarkt am Wallersee Austria.

Asexual reproduction of the new cultivar by terminal stem cuttings since August 2020 in Neumarkt am Wallersee Austria has demonstrated that the new cultivar reproduces true-to-type with all of the characteristics, as herein described, firmly fixed and retained through successive generations of such asexual propagation.

SUMMARY OF THE INVENTION

The following characteristics of the new cultivar have been repeatedly observed and can be used to distinguish 'FLORCUMY05' as a new and distinct cultivar of *Cuphea* plant:

1. Medium purple-colored flowers;
2. Dark green-colored foliage; and
3. Moderately vigorous, upright growth habit.

Plants of the new cultivar differ from plants of the female parent primarily in being earlier to flower and in having a more upright growth habit. Plants of the new cultivar differ from plants of the most likely male parent primarily in having a more purple-colored flower.

Of the many commercially available *Cuphea* cultivars, the most similar in comparison to the new cultivar is MYRTIS Dark Purple 'FLORCUMY01', not patented. However, in comparison, plants of the new cultivar differ from plants of 'FLORCUMY01' in at least the following characteristics:

1. Plants of the new cultivar have less red flower coloration than plants of 'FLORCUMY01'; and
2. Plants of the new cultivar have darker green-colored foliage than plants of 'FLORCUMY01'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'FLORCUMY05'. The approximately three-month-old plants were grown in one-gallon containers for approximately 9 weeks in a greenhouse in Arroyo Grande, California. Plants were given one pinch one week prior to transplant.

DETAILED BOTANICAL DESCRIPTION

Figure 1:
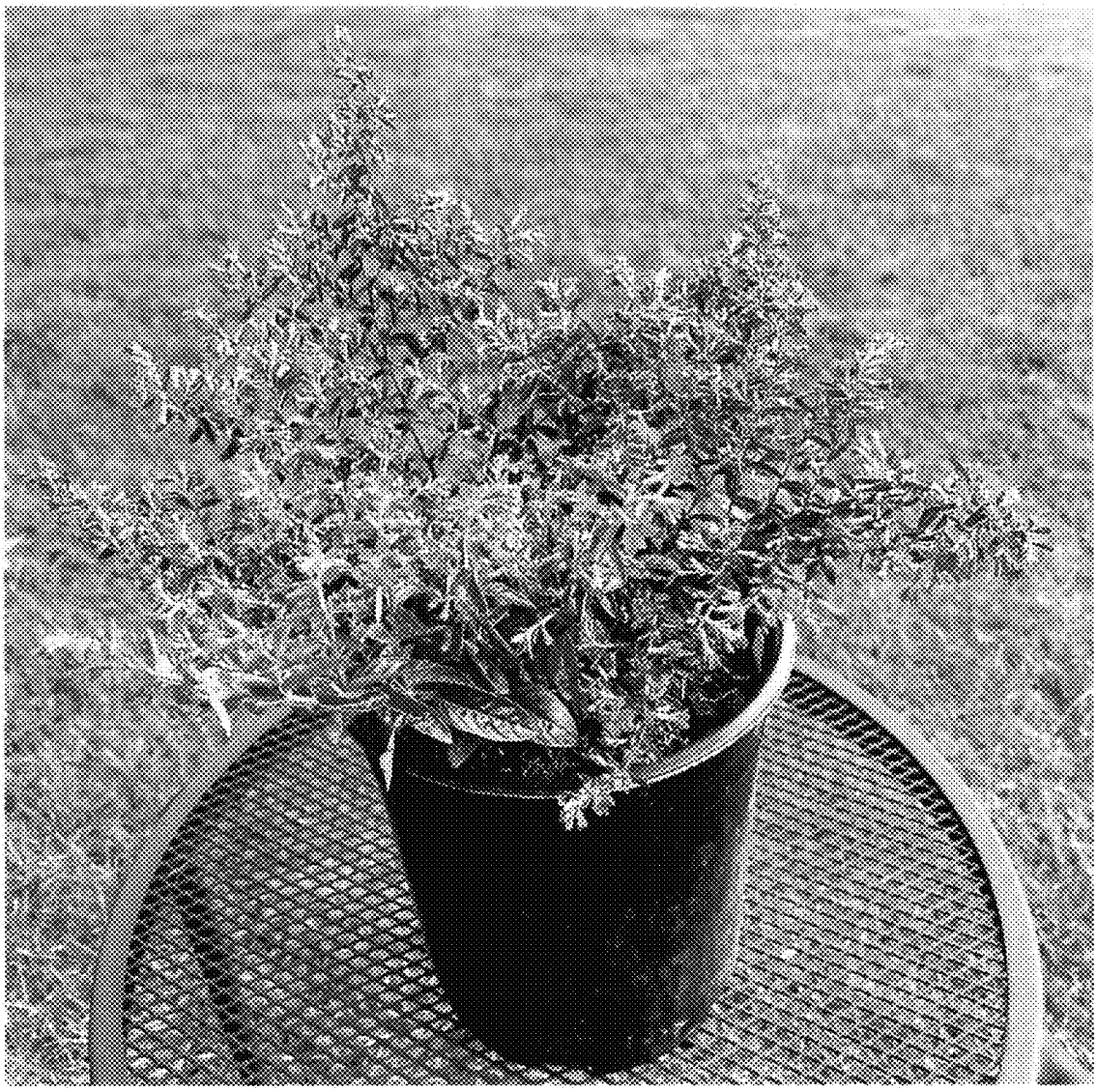
FIG. 1 illustrates a side view of the overall growth and flowering habit of 'FLORCUMY05'.
Figure 2:
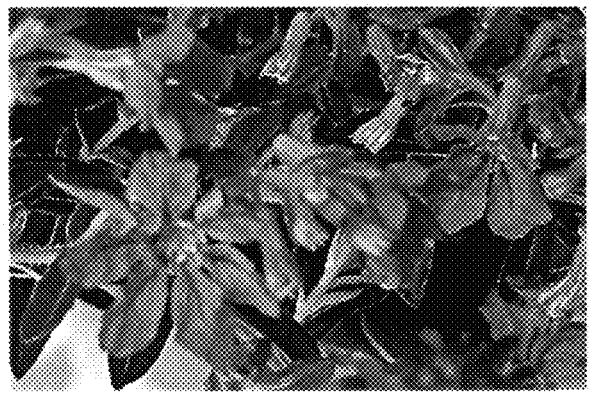
FIG. 2 illustrates a close-up view of an individual flowers of 'FLORCUMY05'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in October 2023 under natural light conditions in Naperville, Illinois.

The following descriptions and measurements describe approximately 3-month-old plants produced from cuttings from stock plants and grown in a polycarbonate-covered greenhouse under conditions comparable to those used in commercial practice. The plants were grown in Arroyo Grande, California in one-gallon containers for approximately 9 weeks utilizing a soilless growth medium. Plants were given one pinch one week prior to transplant. Greenhouse temperatures were maintained at approximately 65° F. to 70° F. (18.3° C. to 21.1° C.). Measurements and numerical values represent averages of typical plants.

Botanical classification: *Cuphea hyssopifolia* 'FLORCUMY05'.

Parentage:

*Female parent.*—'Cupid Purple', not patented.

*Male parent.*—Most likely to be MYRTIS Deep Pink 'FLORCUMY38', not patented.

Propagation:

*Type cutting.*—Terminal stem.

*Time to initiate roots.*—Approximately 10 to 14 days.

*Time to produce a rooted cutting.*—Approximately 28 days.

*Root description.*—Fine, fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, upright growth habit.

*Size.*—Height from soil level to top of plant plane: Approximately 22.0 cm. Width: Approximately 34.0 cm.

*Branching habit.*—Freely branching. Pinching enhances basal branching. Quantity of main branches per plant: Approximately 9.

*Branch.*—Strength: Strong, flexible. Length: Approximately 21.0 cm. Diameter: Approximately 2.0 mm to 3.0 mm. Length of central internode: Approximately 1.5 cm. Texture: Densely pubescent with a mixture of long and short hairs. Color of young stems:146B. Color of mature stems: 146B with a heavy overlay of 187A primarily on upward facing sides.

Foliage description:

*General description.*—Quantity of leaves per main branch: Approximately 20. Fragrance: None detected. Form: Simple. Arrangement: Opposite.

*Leaves.*—Aspect: Perpendicular to obtuse angle to stem. Shape: Lanceolate. Margin: Entire, widely ciliate. Apex: Acute. Base: Rounded. Venation pattern: Pinnate. Length of mature leaf: Approximately 3.0 cm. Width of mature leaf: Approximately 1.2 cm. Texture of upper surface: Glabrous. Texture of lower surface: Sparsely pubescent on venation. Color of upper surface of young and mature foliage: Closest to NN137A with 139A and indistinguishable venation. Color of lower surface of young and mature foliage: Closest to 147B with venation of 145C to indistinguishable.

*Petiole.*—Length: Approximately 1.0 mm. Width: Approximately 1.0 mm. Texture: Sparsely pubescent. Color: 145C.

Flowering description:

*Flowering habit.*—'FLORCUMY05' is freely flowering under outdoor growing conditions with substantially continuous blooming from late spring through late sumer and year-round in greenhouse environment.

*Lastingness of individual flower on the plant.*—Approximately 7 days.

Inflorescence description:

*General Description.*—Type: Terminal and axillary racemes with solitary flowers arising from leaf axils. Quantity per plant: Approximately 115. Fragrance: None detected. Length: Approximately 5.0 cm to 7.0 cm. Width: Approximately 2.0 cm to 2.5 cm. Quantity of fully open flowers per inflorescence: Approximately 1 to 3. Quantity of unopened buds per inflorescence: Approximately 1 to 2.

*Peduncle.*—Strength: Strong, flexible. Aspect: Acute angle to stem. Length: Approximately 1.2 cm. Diameter: Approximately 1.0 mm. Texture: Densely pubescent with a mixture of long and short hairs. Color: 146B with a heavy overlay of 187A primarily on upward facing sides.

Flower description:

*Type.*—Solitary, zygomorphic, tubular with two upper petals and four lower flared petals.

*Bud.*—Rate of opening: Generally takes 3 to 5 days for bud to progress from first color to fully open flower.

*Bud just before opening.*—Shape: Obovoid. Length: Approximately 8.0 mm. Diameter at distal end: Approximately 3.0 mm. Diameter at proximal end: Approximately 2.0 mm. Texture: Calyx portion sparsely pubescent. Color of petal portion: N81A. Color of tube: 144B with venation of 144A.

*Corolla.*—Diameter: Approximately 1.2 cm.

*Petals.*—Quantity: 6, base fused to calyx. Shape: Obovate. Appearance: Matte. Margin: Entire. Apex: Obtuse. Base: Attenuate and fused to calyx. Length: Approximately 5.0 mm. Width: Approximately 3.0 mm. Texture of upper and lower surfaces: Glabrous. Color of upper surface when first and fully open: N81B with N82B and venation of N81A. Color of lower surface when first and fully open: N81B.

*Calyx.*—Fused to form floral tube. Length: Approximately 6.0 mm. Diameter at distal end: Approximately 3.0 mm. Diameter at proximal end: Approximately 2.0 mm. Texture: Calyx portion sparsely pubescent. Texture of inner surface: Tomentose at tube opening. Texture of outer surface: Sparsely pubescent on venation. Color of inner surface: NN155D with two patches of 7B at base of upper petals. Color of outer surface: 144B with venation of 144A.

*Pedicle.*—Strength: Strong, flexible. Aspect: Acute angle to stem. Length: Approximately 6.0 mm. Diameter: Approximately 0.5 mm. Texture: Densely pubescent with a mixture of long and short hairs. Color: 144D.

*Reproductive organs.*—Androecium: Stamen quantity: 11 per flower, base adnate to floral tube. Stamen length: Approximately 6.0 mm. Filament length of free portion: Approximately 3.0 mm. Filament color: NN155D tinted with N81B. Anther shape: Bilobed. Anther length: Approximately 1.0 mm. Anther color: 4C. Pollen amount: Sparse. Pollen color: 4D. Gynoecium: Pistil quantity: 1 per flower. Pistil length: Approximately 5.0 mm. Stigma shape: Club. Stigma length: Less than 1.0 mm. Stigma color: NN155A. Style length: Approximately 2.0 mm. Style color: NN155D tinted with N81B. Ovary length: Approximately 3.0 mm. Ovary color: NN155D.

Seed and fruit production: Neither seed nor fruit production has been observed. Disease and pest resistance: Resistance to pathogens and pests common to *Cuphea* has not been observed.

What is claimed is:

1. A new and distinct cultivar of *Cuphea* plant named 'FLORCUMY05', substantially as herein illustrated and described.

* * * * *